United States Patent
Yoshii et al.

(10) Patent No.: US 10,926,420 B2
(45) Date of Patent: Feb. 23, 2021

(54) MANIPULATOR

(71) Applicant: OLYMPUS CORPORATION, Tokyo (JP)

(72) Inventors: Toshihiro Yoshii, Tokyo (JP); Mitsuaki Hasegawa, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 498 days.

(21) Appl. No.: 15/827,167

(22) Filed: Nov. 30, 2017

(65) Prior Publication Data

US 2018/0079089 A1 Mar. 22, 2018

Related U.S. Application Data

(63) Continuation of application No. PCT/JP2016/065950, filed on May 31, 2016.

(30) Foreign Application Priority Data

Jul. 17, 2015 (JP) .............................. JP2015-143122

(51) Int. Cl.
*B25J 17/02* (2006.01)
*B25J 18/06* (2006.01)
(Continued)

(52) U.S. Cl.
CPC ................ *B25J 17/02* (2013.01); *A61B 17/28* (2013.01); *A61B 34/30* (2016.02); *B25J 9/10* (2013.01);
(Continued)

(58) Field of Classification Search
CPC ..... B25J 17/02; B25J 9/10; B25J 9/104; B25J 18/06; A61B 34/30; A61B 17/28; A61B 2034/301; A61B 2090/064
See application file for complete search history.

(56) References Cited

U.S. PATENT DOCUMENTS

2005/0049616 A1   3/2005   Rivera et al.
2005/0090837 A1   4/2005   Sixto, Jr. et al.
(Continued)

FOREIGN PATENT DOCUMENTS

CN   101444415 A    6/2009
EP   1 607 050 A1  12/2005
(Continued)

OTHER PUBLICATIONS

Extended Supplementary European Search Report dated Feb. 11, 2019 in European Patent Application No. 16 82 7506.3.
(Continued)

*Primary Examiner* — Zakaria Elahmadi
(74) *Attorney, Agent, or Firm* — Scully, Scott, Murphy & Presser, P.C.

(57) ABSTRACT

A manipulator including: an end effector movable about a joint; a motor configured to generate force so as to move the end effector; a wire for transmitting the force from the motor to the end effector; a guide member connected between the end effector and motor. The guide member including: a guide tube comprising at least one lumen extended in a longitudinal direction, the lumen configured to guide the wire; and an outer sheath configured to cover the guide tube in a longitudinal direction and to move relative to the motor in the longitudinal direction, the outer sheath having a rigidity higher than the guide tube. The manipulator further including an adjusting mechanism configured to adjust a position of the proximal end section of the outer sheath relative to the motor in the longitudinal direction of the guide tube so as to adjust a tensile-force generated on the wire.

4 Claims, 14 Drawing Sheets

(51) Int. Cl.
    *A61B 34/30*     (2016.01)
    *A61B 17/28*     (2006.01)
    *B25J 9/10*      (2006.01)
    *A61B 90/00*     (2016.01)

(52) U.S. Cl.
    CPC .............. *B25J 9/104* (2013.01); *B25J 18/06*
        (2013.01); *A61B 2034/301* (2016.02); *A61B*
        *2090/064* (2016.02)

(56) References Cited

U.S. PATENT DOCUMENTS

| | | | |
|---|---|---|---|
| 2005/0277951 A1 | 12/2005 | Smith et al. | |
| 2005/0277952 A1 | 12/2005 | Arp et al. | |
| 2005/0277953 A1 | 12/2005 | Francese et al. | |
| 2005/0277955 A1 | 12/2005 | Palmer et al. | |
| 2005/0277956 A1 | 12/2005 | Francese et al. | |
| 2008/0045786 A2 | 2/2008 | Smith et al. | |
| 2008/0051808 A1 | 2/2008 | Rivera et al. | |
| 2008/0058861 A1* | 3/2008 | Cooper | A61B 34/70 606/205 |
| 2008/0064921 A1* | 3/2008 | Larkin | A61B 1/05 600/104 |
| 2008/0167665 A1 | 7/2008 | Arp et al. | |
| 2008/0243064 A1 | 10/2008 | Stahler et al. | |
| 2008/0249536 A1* | 10/2008 | Stahler | A61B 34/71 606/130 |
| 2008/0262480 A1 | 10/2008 | Stahler et al. | |
| 2008/0262513 A1 | 10/2008 | Stahler et al. | |
| 2009/0112230 A1 | 4/2009 | Jinno | |
| 2009/0138025 A1* | 5/2009 | Stahler | A61B 34/71 606/130 |
| 2009/0143642 A1 | 6/2009 | Takahashi et al. | |
| 2009/0171151 A1* | 7/2009 | Choset | A61B 34/20 600/114 |
| 2010/0076451 A1 | 3/2010 | Zwolinski et al. | |
| 2011/0071508 A1* | 3/2011 | Duval | A61B 1/00087 606/1 |
| 2011/0071564 A1* | 3/2011 | Suzuki | A61B 17/29 606/205 |
| 2012/0271327 A1 | 10/2012 | West et al. | |
| 2013/0006287 A1 | 1/2013 | West et al. | |
| 2013/0218005 A1* | 8/2013 | Desai | A61B 17/00234 600/424 |
| 2013/0289617 A1* | 10/2013 | Suzuki | A61B 17/2909 606/205 |
| 2014/0249545 A1* | 9/2014 | Hyodo | A61B 34/30 606/130 |
| 2014/0296869 A1* | 10/2014 | Kernbaum | B29C 48/09 606/130 |
| 2015/0141756 A1* | 5/2015 | Cheng | A61B 1/00078 600/146 |
| 2015/0196313 A1 | 7/2015 | Ishida et al. | |
| 2015/0366572 A1* | 12/2015 | Sholev | A61B 17/32 606/170 |
| 2016/0235486 A1* | 8/2016 | Larkin | B25J 9/1671 |
| 2016/0279388 A1* | 9/2016 | Barrish | A61M 25/0155 |
| 2016/0287346 A1 | 10/2016 | Hyodo et al. | |
| 2017/0095234 A1* | 4/2017 | Prisco | A61B 17/3478 |
| 2017/0095922 A1* | 4/2017 | Licht | A61B 34/30 |
| 2017/0325904 A1* | 11/2017 | Hyodo | A61B 34/73 |
| 2018/0001058 A1* | 1/2018 | Schlesinger | A61M 25/0147 |
| 2018/0215051 A1* | 8/2018 | Kan | B25J 9/104 |

FOREIGN PATENT DOCUMENTS

| | | |
|---|---|---|
| EP | 1 607 052 A2 | 12/2005 |
| EP | 1 607 053 A1 | 12/2005 |
| EP | 1 607 054 A2 | 12/2005 |
| EP | 1 607 055 A1 | 12/2005 |
| EP | 1 607 056 A1 | 12/2005 |
| EP | 1 607 057 A1 | 12/2005 |
| EP | 2 064 984 A2 | 6/2009 |
| EP | 2 077 095 A2 | 7/2009 |
| EP | 2 151 201 A1 | 2/2010 |
| EP | 2 213 221 A1 | 8/2010 |
| EP | 2 810 607 A1 | 12/2014 |
| EP | 2 901 956 A1 | 8/2015 |
| EP | 3 085 324 A1 | 10/2016 |
| JP | 8-286123 A | 11/1996 |
| JP | 2006-000634 A | 1/2006 |
| JP | 2006-000635 A | 1/2006 |
| JP | 2006-000637 A | 1/2006 |
| JP | 2006-000638 A | 1/2006 |
| JP | 2006-000639 A | 1/2006 |
| JP | 2006-000640 A | 1/2006 |
| JP | 2006-000641 A | 1/2006 |
| JP | 2009-107087 A | 5/2009 |
| JP | 2010-46384 A | 3/2010 |
| JP | 2010-221329 A | 10/2010 |
| JP | 2012-504016 A | 2/2012 |
| JP | 2013-103074 A | 5/2013 |
| JP | 2014-64755 A | 4/2014 |
| JP | 2014-159071 A | 9/2014 |
| WO | 2008/101228 A2 | 8/2008 |
| WO | 2010/033478 A1 | 3/2010 |
| WO | 2010/039387 A1 | 4/2010 |
| WO | 2013/073713 A1 | 5/2013 |
| WO | 2015/093602 A1 | 6/2015 |

OTHER PUBLICATIONS

International Search Report dated Aug. 9, 2016 received in PCT/JP2016/065950.

* cited by examiner

MANIPULATOR

CROSS-REFERENCE TO RELATED APPLICATIONS

This application is a continuation of International Application PCT/JP2016/065950 filed on May 31, 2016, which is hereby incorporated by reference herein in its entirety. This application is based on Japanese Patent Application No. 2015-143122 filed on Jul. 17, 2015, the contents of which are incorporated herein by reference.

BACKGROUND

Field

The present disclosure relates to manipulators.

Prior Art

A known surgical device in the related art uses a wire to drive a bending section or a movable section, such as forceps, disposed at the distal end of a flexible insertion section (for example, see Publication of Japanese Patent No. 5542288).

The surgical device according to Japanese Patent No. 5542288 includes a constant-force spring that applies a fixed initial tensile force to the wire so as to prevent the tensile force of the wire, which extends internally through the flexible insertion section, from changing due to bending of the flexible insertion section.

SUMMARY

Accordingly, a manipulator is provided. The manipulator comprising: an end effector movable about a joint; a motor configured to generate force so as to move the end effector about the joint; a wire configured to transmit the force from the motor to the end effector; a guide member connected between the end effector and motor, the guide member comprises: a guide tube comprising at least one lumen extended in a longitudinal direction, the at least one lumen configured to guide the wire; and an outer sheath configured to cover the guide tube in a longitudinal direction and to move relative to the motor in the longitudinal direction of the guide tube, the outer sheath having a rigidity higher than a rigidity of the guide tube; and an adjusting mechanism configured to adjust a position of the proximal end section of the outer sheath relative to the motor in the longitudinal direction of the guide tube so as to adjust a tensile-force generated on the wire.

DETAILED DESCRIPTION

A manipulator 1 according to an embodiment will be described below with reference to the drawings.

Figure 1:
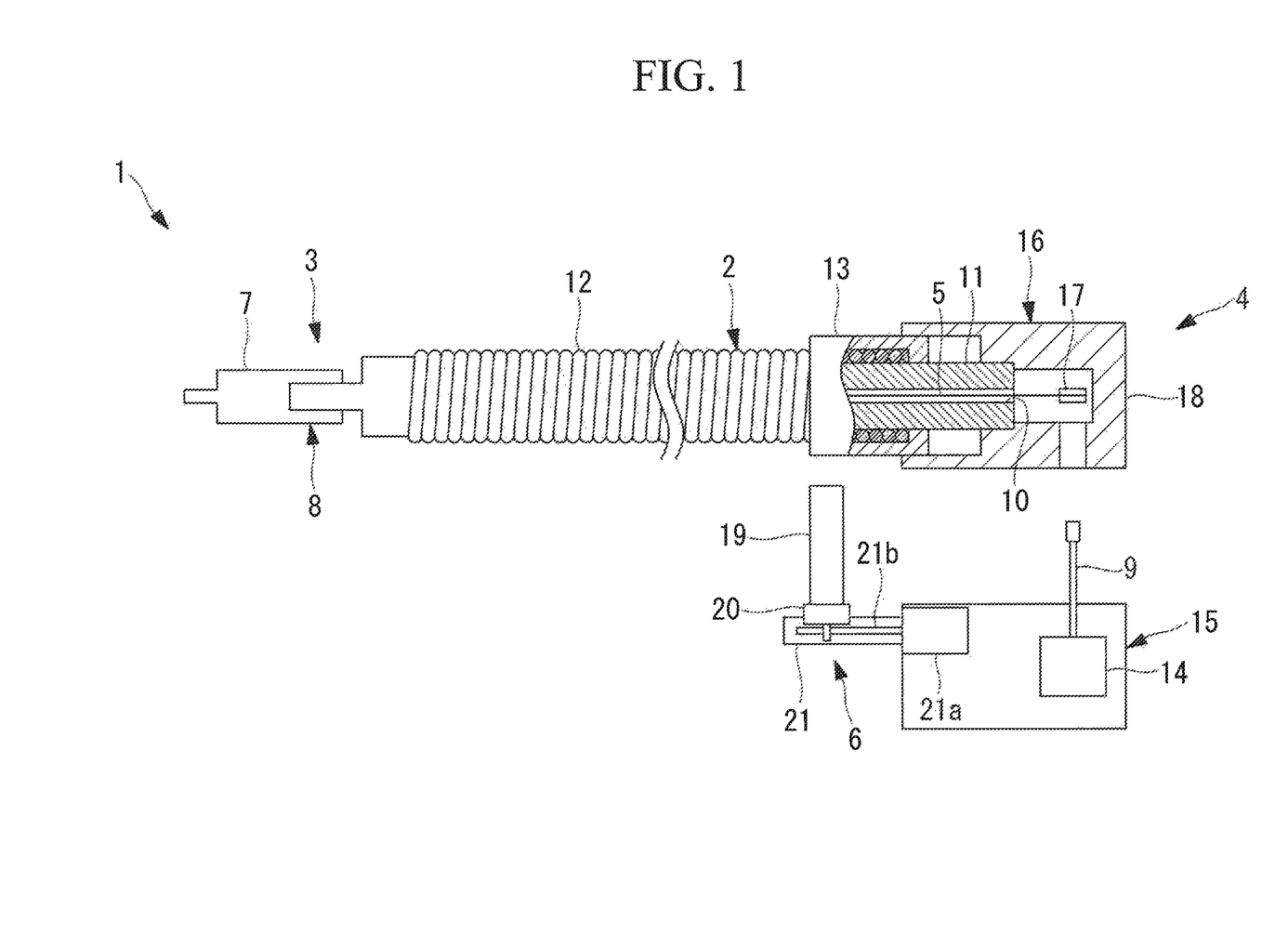
FIG. 1 is a vertical-sectional partially-cutaway view of a manipulator according to an embodiment.

For example, as shown in FIG. 1, the manipulator 1 according to this embodiment includes a long guide member 2 that is elongate and flexible and that is to be inserted into the body cavity of a patient through a channel of an endoscope to be inserted into the body cavity of the patient, a movable section 3 (end effector) disposed at the distal end of the long guide member 2, a driving section 4 that is disposed at the proximal end of the long guide member 2 and that actuates the movable section 3, wires (tensile-force transmitting members) 5 that transmit a driving force generated by the driving section 4 as a tensile force to the movable section 3, and a tensile-force adjusting mechanism 6 that adjusts the tensile force of the wires 5.

The movable section 3 includes a treatment section 7, such as forceps, to be applied to an affected site inside the body and also includes at least one joint section 8 that supports the treatment section 7. For simplifying the description, the example shown in the drawings illustrates a case where the joint section 8 has a single swiveling joint that causes the treatment section 7 to swivel about an axis orthogonal to the longitudinal axis of the long guide member 2.

The long guide member 2 includes a multi-lumen tube (guide tube) 11 having two lumens 10 through which two wires 5 extend, a coil tube (outer sheath) 12 disposed so as to cover the outer peripheral surface of the multi-lumen tube 11, and a movable end member (proximal end section) 13 that is fixed to the proximal end of the coil tube 12 and that is movable in the longitudinal direction of the multi-lumen tube 11.

The multi-lumen tube 11 is composed of a readily-deformable flexible resin material having low rigidity. In contrast, the coil tube 12 is composed of a metallic material having higher rigidity than the multi-lumen tube 11. As shown in FIG. 1, the coil tube 12 is a tightly-wound coil in which elemental wires are closely in contact with each other without gaps therebetween in a state where the long guide member 2 extends straight.

The driving section 4 includes a motor unit 15 equipped with a motor 14, and also includes a manipulator-side driving section 16 attached to the proximal end of the multi-lumen tube 11. The motor unit 15 and the manipulator-side driving section 16 are attachable to and detachable from each other. The manipulator-side driving section 16 includes a pulley (power converting section) 17 around which the two wires 5 are routed, and also includes a housing 18 that rotatably supports the pulley 17.

When the manipulator-side driving section 16 is coupled to the motor unit 15, a shaft 9 of the motor 14 in the motor unit 15 and the pulley 17 of the manipulator-side driving section 16 are coupled to each other by means of, for example, a spline gear. Thus, a rotational driving force of the motor 14 is converted into a tensile force of either one of the wires 5 routed around the pulley 17, depending on the rotational direction of the pulley 17. Then, the joint section 8 is driven in either direction by the tensile force transmitted by the wire 5.

The distal end of the multi-lumen tube 11 is fixed to the joint section 8, whereas the proximal end of the multi-lumen tube 11 is fixed to the housing 18 of the manipulator-side driving section 16. The distal end of the coil tube 12 is also fixed to the joint section 8.

Furthermore, as shown in FIG. 1, in the state where the long guide member 2 extends straight, a gap is formed between the movable end member 13 and the housing 18 in the longitudinal direction of the multi-lumen tube 11.

The tensile-force adjusting mechanism 6 includes a slider 20 that is provided in the motor unit 15 and that has a connection section 19 to be fixed to the movable end member 13 when the motor unit 15 is coupled to the manipulator-side driving section 16, and also includes a movement mechanism 21 that moves the slider 20 in the longitudinal direction of the multi-lumen tube 11.

The movement mechanism 21 is, for example, a linear motion mechanism equipped with a motor 21a and a ball screw (shaft) 21b.

Figure 2A:
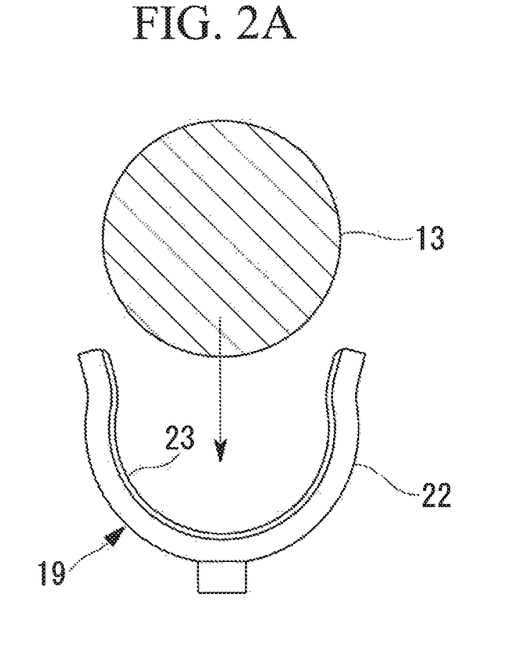
FIG. 2A is a front view illustrating a state where a slider and a connection section included in the manipulator in FIG. 1 are separated from each other.
Figure 2B:
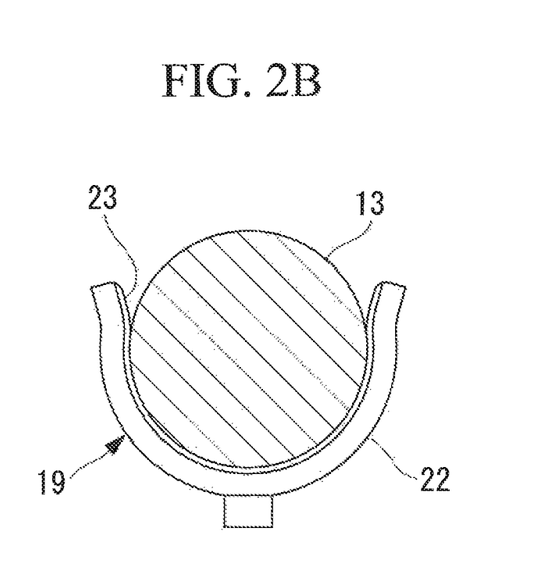
FIG. 2B is a front view illustrating a state where the slider and the connection section included in the manipulator in FIG. 1 are coupled to each other.

For example, as shown in FIGS. 2A and 2B, the connection section 19 may employ a substantially cross-sectionally C-shaped gripping member 22 that is brought into contact with the movable end member 13, which has a cylindrical shape, from the radially outer side thereof and accommodates the movable end member 13 so as to cover substantially half the circumference of the outer peripheral surface of the movable end member 13. In the drawings, reference sign 23 denotes a coating composed of a friction-increasing material.

When the connection section 19 accommodates the movable end member 13, the movable end member 13 is tightened radially inward by the elasticity of the connection section 19, and the connection section 19 becomes secured to the movable end member 13 by friction in the contact area between the two.

The following description relates to a case where medical treatment is performed inside the body of the patient by using the manipulator 1 according to this embodiment having the above-described configuration.

The manipulator 1 according to this embodiment is inserted through a channel of an insertion section of an endoscope inserted into the body cavity from outside the body of a patient, starting from the movable section 3 at the distal end. The movable section 3 is then made to protrude from an opening of a forceps channel in a distal-end surface of the insertion section of the endoscope disposed inside the body.

In this case, the body cavity is often curved, so that the insertion section of the endoscope and the channel provided at the insertion section are inserted into the body cavity by being bent in conformity to the shape of the body cavity. Therefore, when the manipulator 1 is to be inserted through such a channel, the manipulator 1 would be inserted while bending the long guide member 2 in conformity to the channel.

In the case where the long guide member 2 of the manipulator 1 according to this embodiment is to be bent, the multi-lumen tube 11 having high flexibility and disposed along the center is bent. Since the opposite ends of the multi-lumen tube 11 are fixed to the movable section 3 and the driving section 4, if the multi-lumen tube 11 is bent without increasing or decreasing the length along the center line thereof, the lumens 10 formed in the multi-lumen tube 11 do not significantly expand or contract. As a result, the path length of the wires 5 disposed within the lumens 10 do not significantly change.

When the multi-lumen tube 11 is bent, the coil tube 12 covering the outer periphery thereof is also bent. Because the coil tube 12 is composed of a material having rigidity high enough for the multi-lumen tube 11, when the long guide member 2 is bent, the length of an area thereof disposed at the radially inner side of the bend does not change such that the elemental wires are kept closely in contact with each other, whereas the elemental wires in an area disposed at the radially outer side of the bend become separated by an increased distance.

Figure 4A:
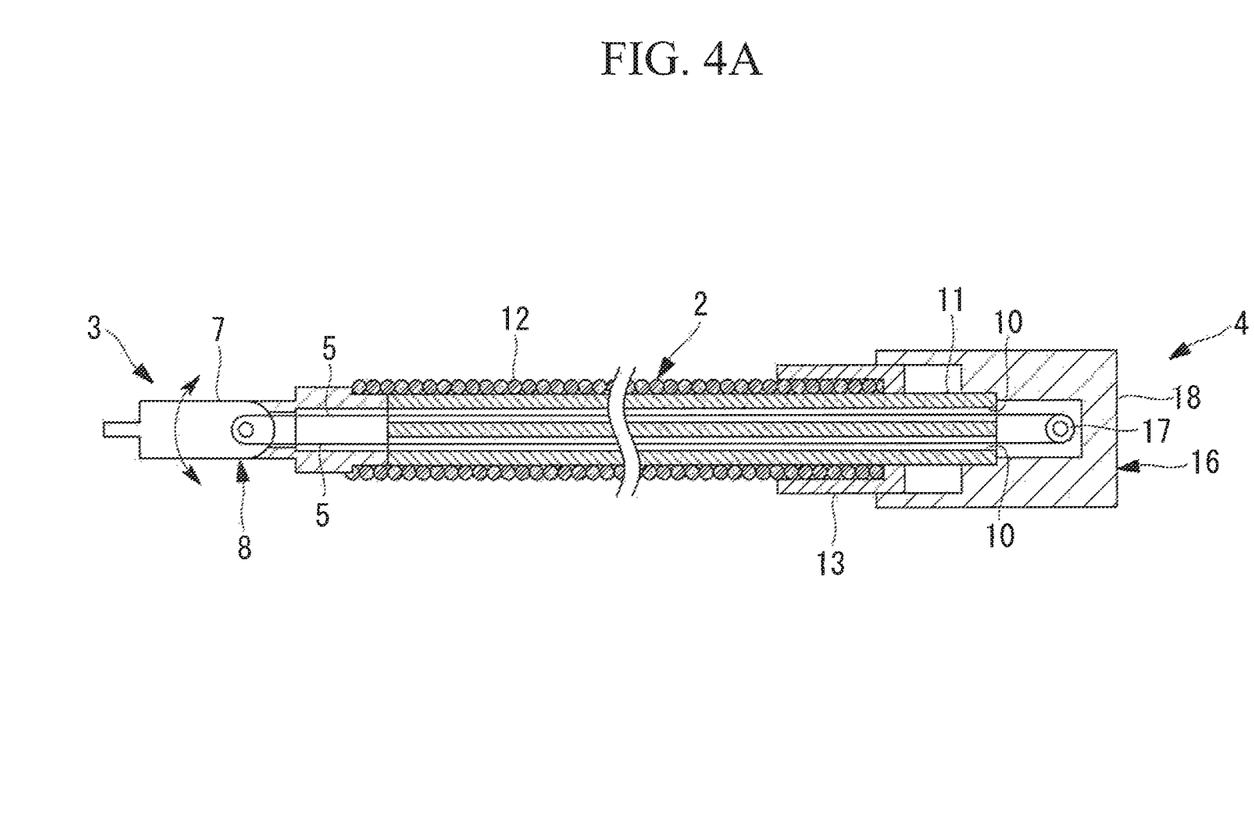
FIG. 4A is a vertical sectional view illustrating a state where a long guide member of the manipulator in FIG. 1 extends straight.
Figure 4B:
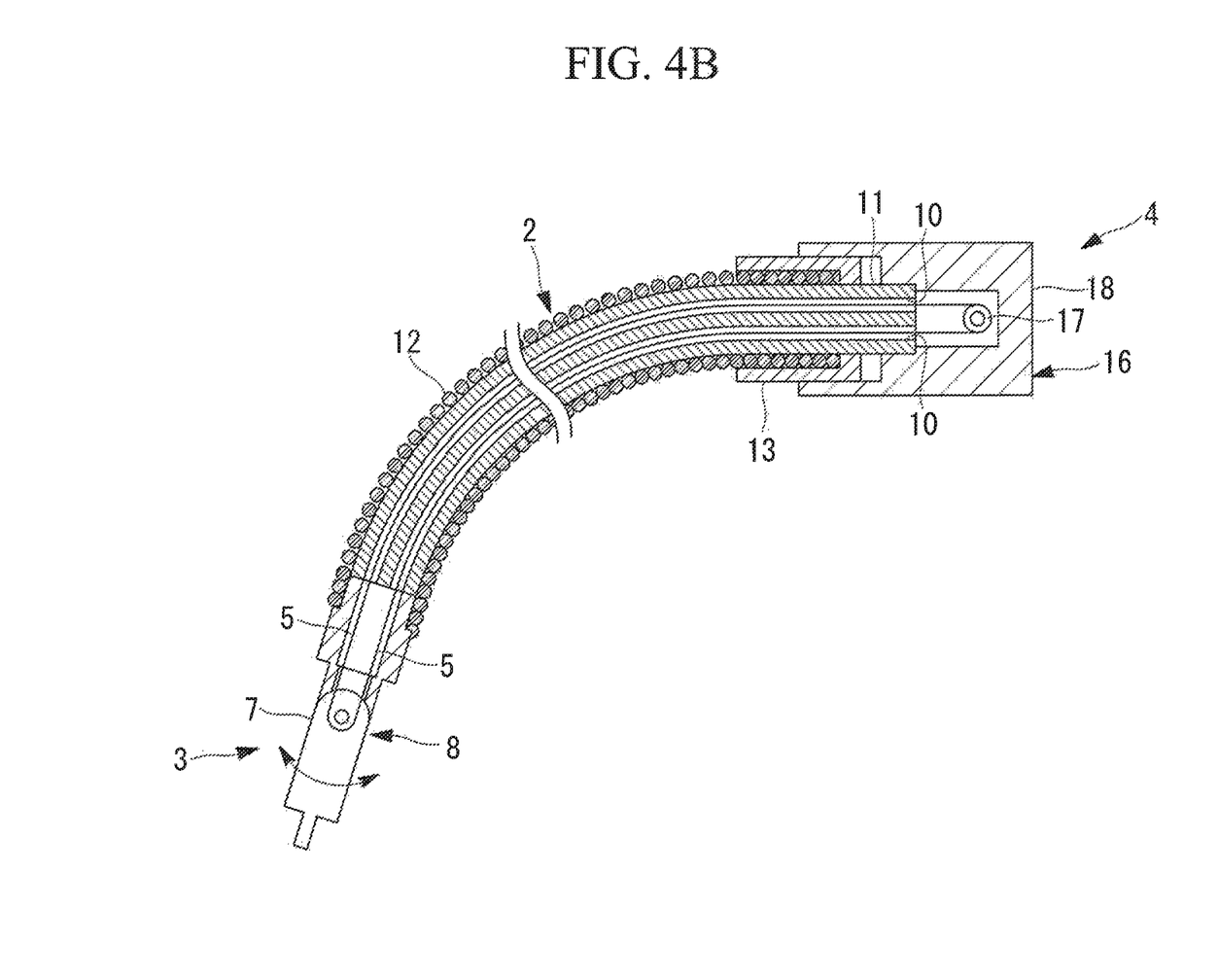
FIG. 4B is a vertical sectional view illustrating a state where the long guide member of the manipulator in FIG. 1 is bent.

As shown in FIG. 4A, in the manipulator 1 according to this embodiment, the proximal end of the coil tube 12 is fixed to the movable end member 13 that is movable relative to the housing 18 of the driving section 4 in the longitudinal direction of the multi-lumen tube 11. Therefore, as shown in FIG. 4B, when the long guide member 2 is bent, the movable end member 13 moves relative to the housing 18, thus causing the proximal end of the coil tube 12 to move toward the driving section 4. Specifically, when the long guide member 2 is bent, the proximal end of the coil tube 12 shifts so as to close the gap between the movable end member 13 and the housing 18 since the proximal end of the coil tube 12 is not fixed. As a result, the length of the multi-lumen tube 11 is maintained, and the path length of the wires 5 is prevented from increasing.

Figure 3:
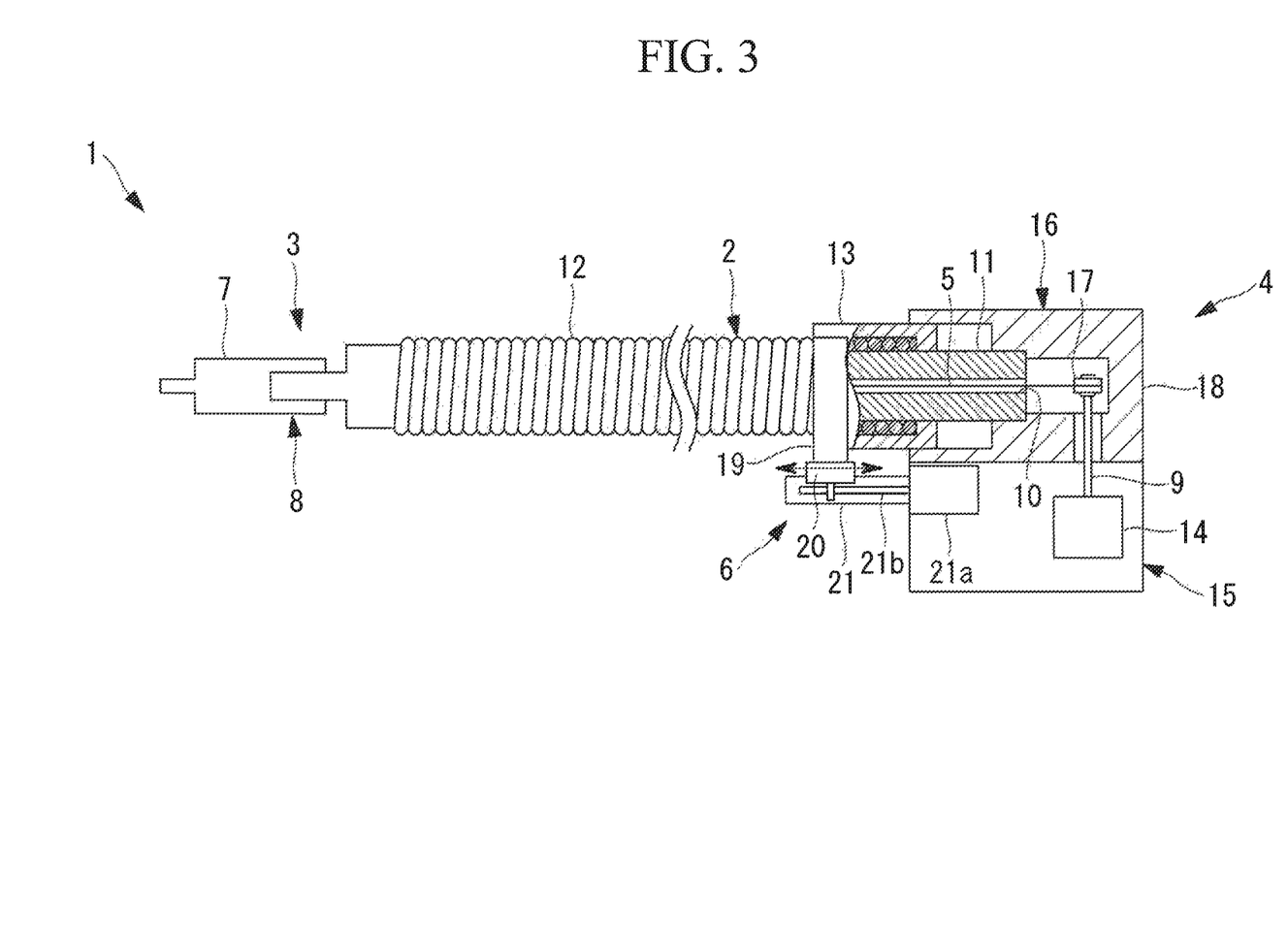
FIG. 3 is a vertical-sectional partially-cutaway view illustrating a state where a motor unit is coupled to a manipulator-side driving section of the manipulator in FIG. 1.

Subsequently, in this state where the long guide member 2 is bent and the movable section 3 protrudes from the distal end of the insertion section of the endoscope near the affected site, the manipulator-side driving section 16 included in the driving section 4 is attached to the motor unit 15. Consequently, as shown in FIG. 3, the shaft 9 of the motor 14 included in the motor unit 15 becomes connected to the pulley 17 of the manipulator-side driving section 16, and the connection section 19 provided in the slider 20 of the tensile-force adjusting mechanism 6 becomes fixed to the movable end member 13.

When the motor 14 of the motor unit 15 is actuated in this state, the rotational force of the motor 14 is transmitted to the pulley 17 and is converted into a tensile force of the wires 5 by the pulley 17. The tensile force of either one of the wires 5 increases so that the movable section 3 is operated.

In this case, in the manipulator 1 according to this embodiment, the connection section 19 provided in the slider 20 of the tensile-force adjusting mechanism 6 is fixed to the movable end member 13 of the coil tube 12, so that, by applying a tensile force to the wire 5 for driving the movable section 3, a compression force applied to the multi-lumen tube 11 can be reduced.

Furthermore, by moving the slider 20 by actuating the motor 21a of the movement mechanism 21, the position of the proximal end of the coil tube 12 relative to the multi-lumen tube 11 can be adjusted in the longitudinal direction of the multi-lumen tube 11. Specifically, by moving the slider 20 toward the distal end of the multi-lumen tube 11, the movable section 3 is made to advance forward so that the initial tensile force applied to the wire 5 can be increased. In contrast, by moving the slider 20 toward the proximal end of the multi-lumen tube 11, the movable section 3 is made to retract so that the initial tensile force applied to the wire 5 can be reduced.

Accordingly, the manipulator 1 according to this embodiment is advantageous in that the position of the proximal end of the coil tube 12 can be adjusted by actuating the movement mechanism 21, so that the tensile force of the wire 5 can be adjusted and an appropriate tensile force can be applied thereto in accordance with the bent state of the long guide member 2, whereby the movable section 3 can be operated with high accuracy.

Although the multi-lumen tube 11 is composed of a material having low rigidity in this embodiment, the rigidity of the long guide member 2 itself is increased by means of the coil tube 12 that covers the outer periphery of the multi-lumen tube 11. Therefore, by causing a force to act on the proximal end of the coil tube 12 in the longitudinal direction, the entire manipulator 1 can be made to advance or retract. In addition, by applying torque to the proximal end of the coil tube 12 about the longitudinal axis, the movable section 3 at the distal end can be rotated about the longitudinal axis.

Figure 5:
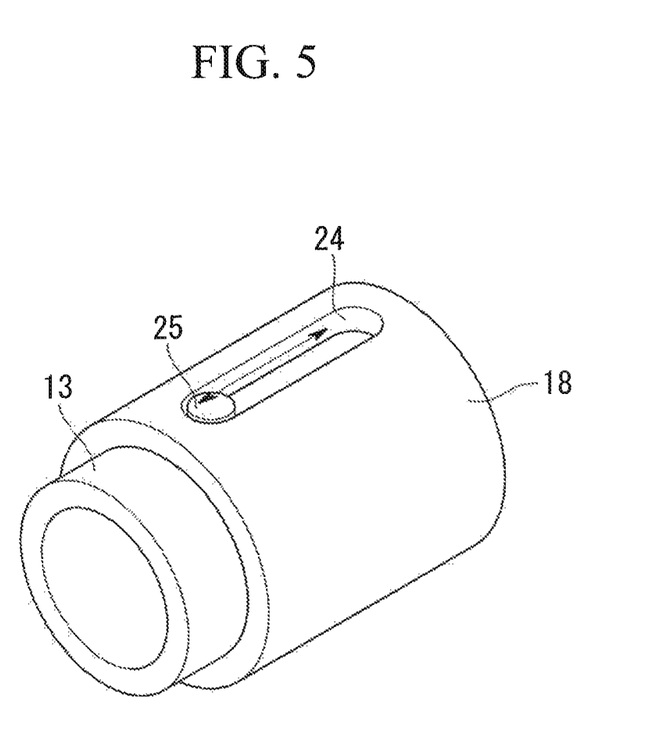
FIG. 5 illustrates a modification of the manipulator in FIG. 1 and is a perspective view showing a rotation stopper.

In addition to the method of applying torque directly to the proximal end of the coil tube 12, the method for applying torque to the coil tube 12 may involve providing a rotation stopper that regulates displacement of the movable end member 13 in the circumferential direction between the housing 18 and the movable end member 13 and transmitting the torque to be applied to the housing 18 to the coil tube 12 via the rotation stopper, as shown in FIG. 5.

The rotation stopper may be constituted by providing the housing 18 with a long hole 24 extending in the longitudinal direction of the multi-lumen tube 11 and providing the movable end member 13 with a pin 25 fitted in the long hole 24. When the slider 20 is to move in the longitudinal direction of the multi-lumen tube 11, the long hole 24 is moved relative to the pin 25. When torque is applied to the housing 18, torque acting around the longitudinal axis of the multi-lumen tube 11 can be transmitted in accordance with the engagement between the pin 25 and the long hole 24.

Figure 6A:
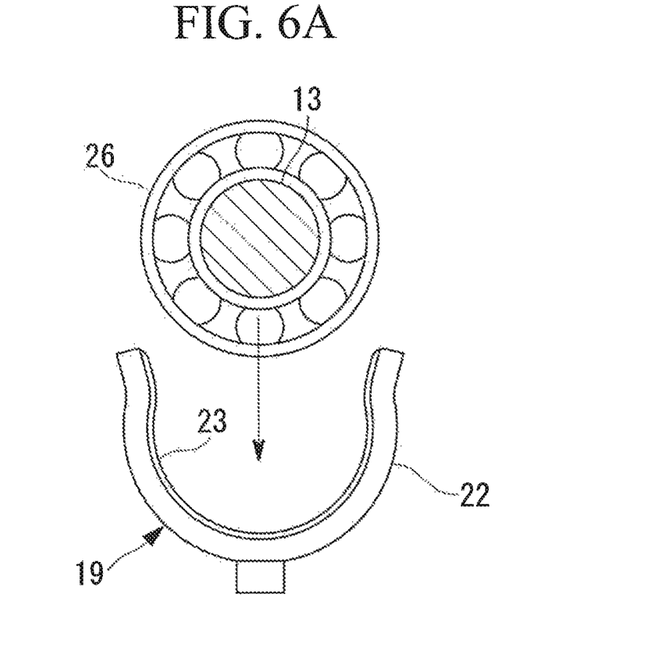
FIG. 6A illustrates a modification of the manipulator in FIG. 1 and is a front view illustrating a separated state of a connection section different from the connection section in FIGS. 2A and 2B.
Figure 6B:
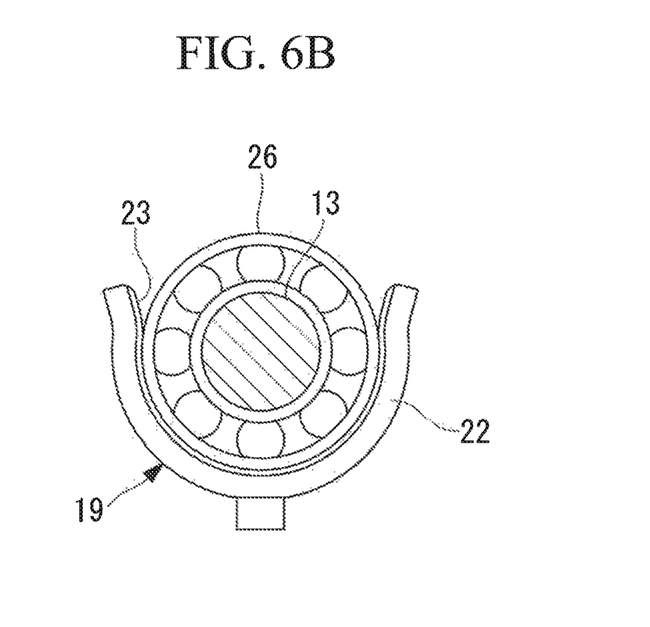
FIG. 6B illustrates a modification of the manipulator in FIG. 1 and is a front view illustrating a coupled state of the connection section different from the connection section in FIGS. 2A and 2B.

As shown in FIGS. 6A and 6B, the connection section 19 that connects the slider 20 to the movable end member 13 provided at the proximal end of the coil tube 12 may have a structure in which an outer ring of a bearing 26 fixed to the movable end member 13 is engaged with the inner side of the C-shaped gripping member 22 such that the movable end member 13 is prevented from moving in the longitudinal direction of the multi-lumen tube 11 while the movable end member 13 is allowed to rotate relative to the slider 20.

Figure 7A:
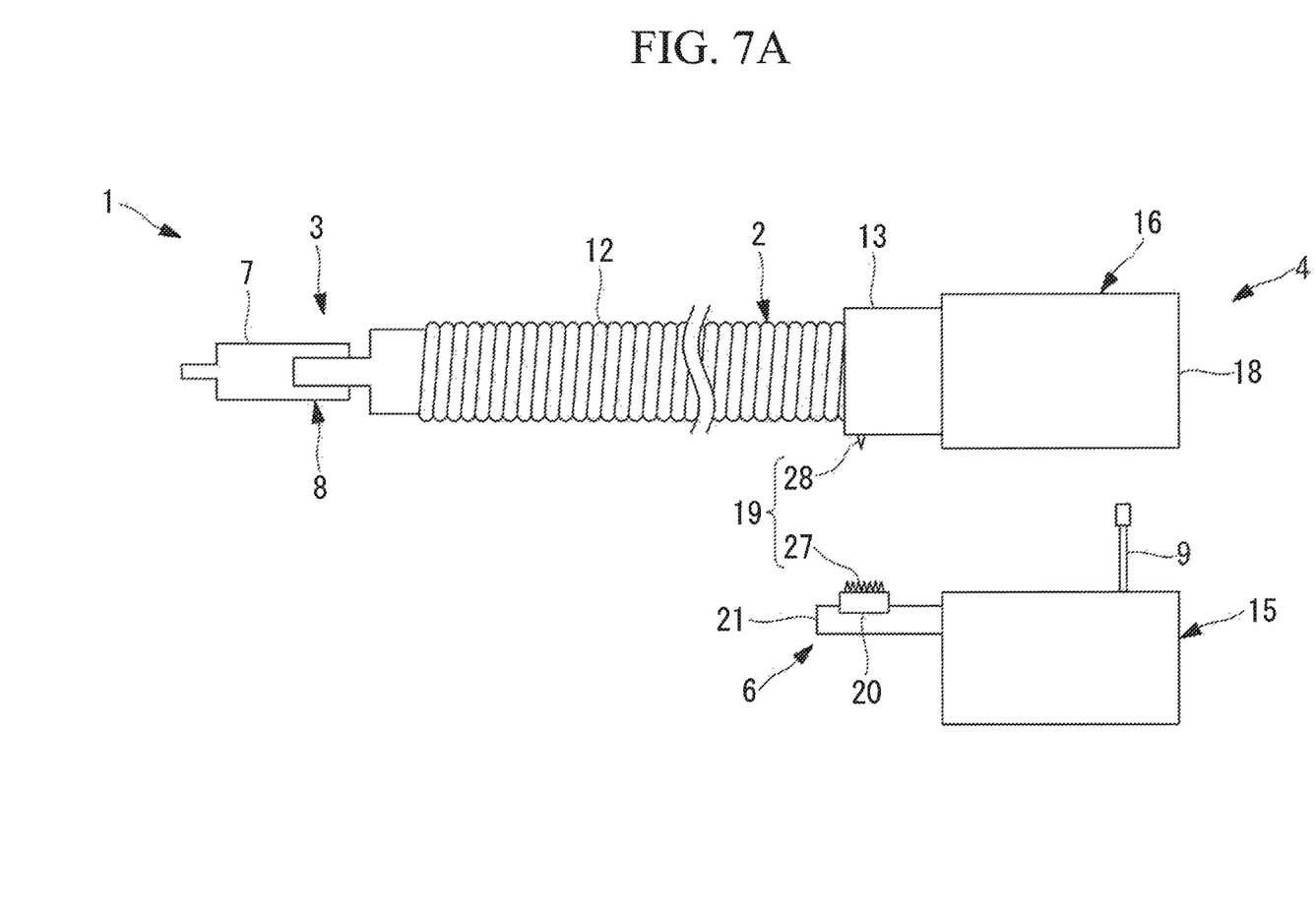
FIG. 7A is a side view illustrating a separated state of another type of connection section in FIG. 1.
Figure 7B:
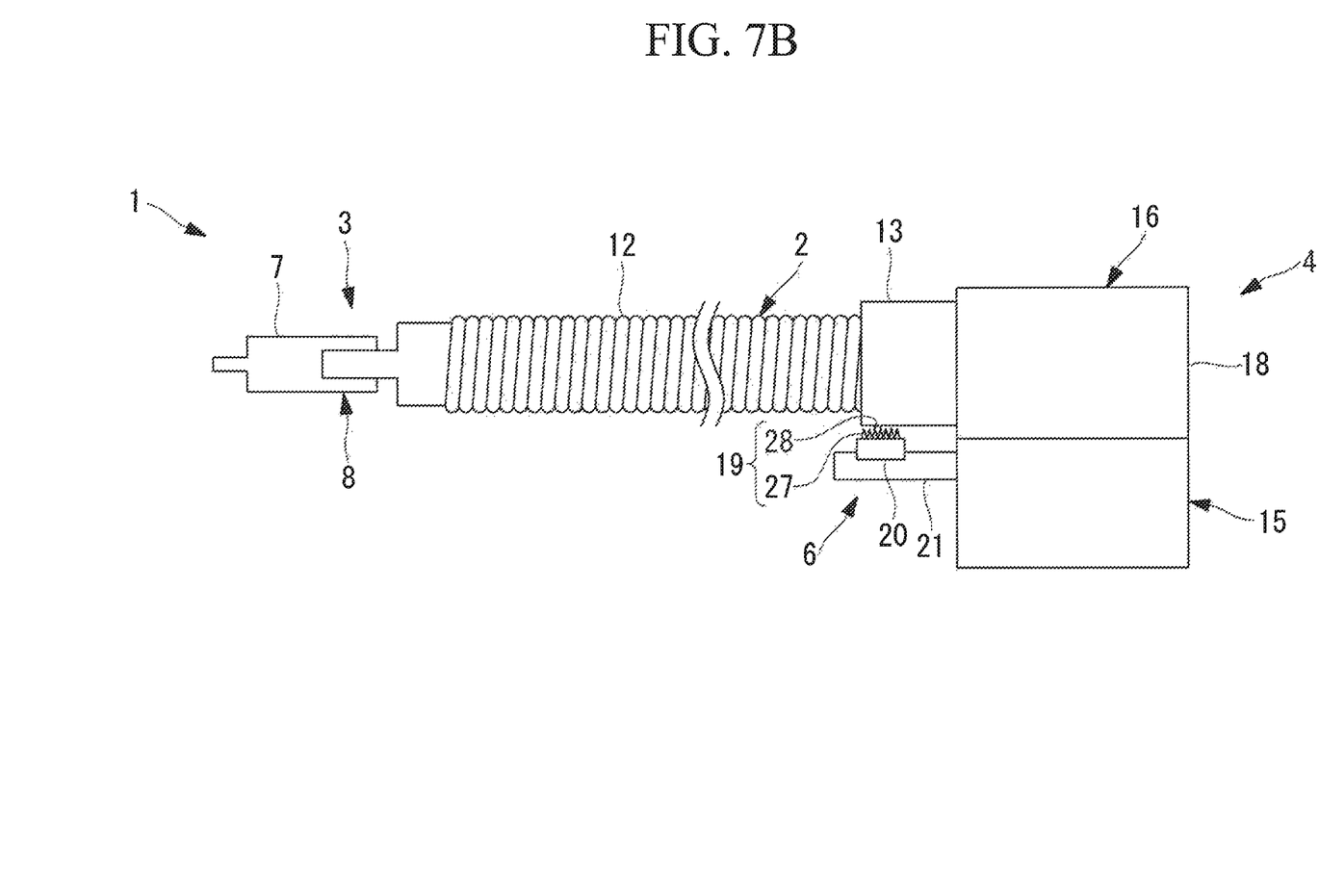
FIG. 7B is a side view illustrating a coupled state of another type of connection section in FIG. 1.

Furthermore, as shown in FIGS. 7A and 7B, the connection section 19 may be constituted of a plurality of grooves 27 arranged side-by-side on the slider 20 in the moving direction thereof and a protrusion 28 provided on the movable end member 13. When the manipulator-side driving section 16 is attached to the motor unit 15, the protrusion 28 of the movable end member 13 is engaged with any of the grooves 27 in the slider 20 so that relative movement between the movable end member 13 and the slider 20 can be restricted at a freely-chosen position. The protrusion 28 and the grooves 27 may be interchanged with each other.

Figure 8A:
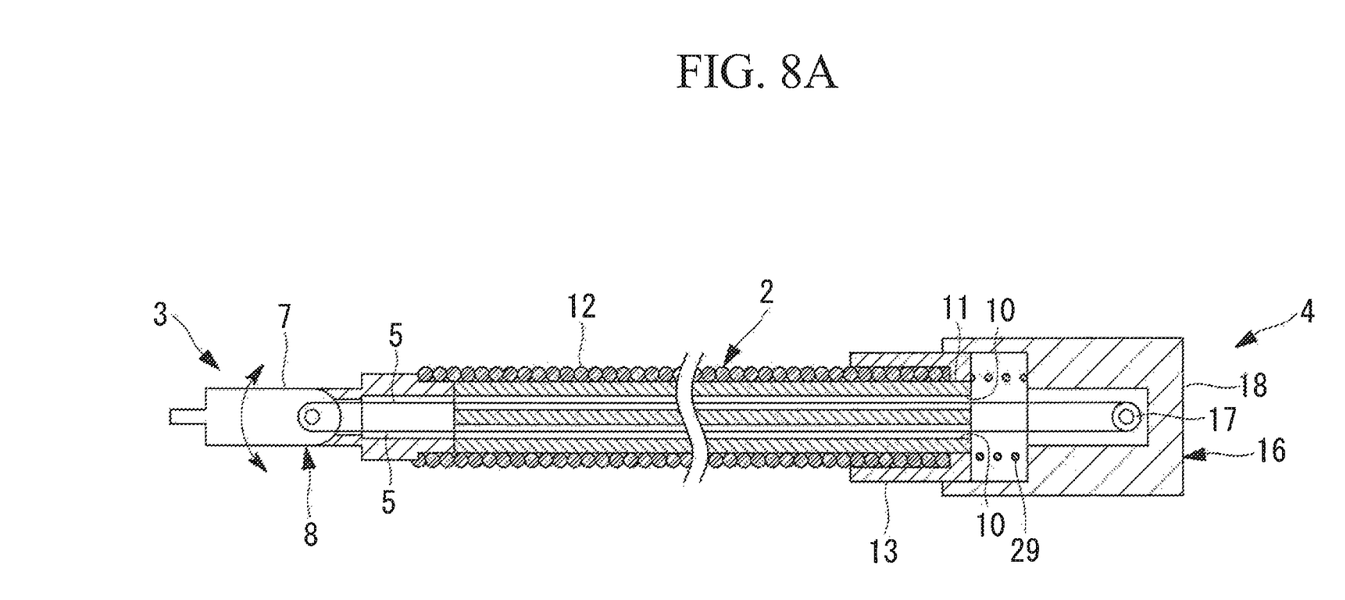
FIG. 8A illustrates another modification of the manipulator in FIG. 1 and is a vertical sectional view showing a state where the manipulator extends straight.

As an alternative to this embodiment in which the proximal end of the multi-lumen tube 11 is fixed to the housing 18, the proximal end of the multi-lumen tube 11 may be fixed to the slider 20, and a compression spring 29 may be disposed between the housing 18 and the slider 20, as shown in FIG. 8A.

Figure 8B:
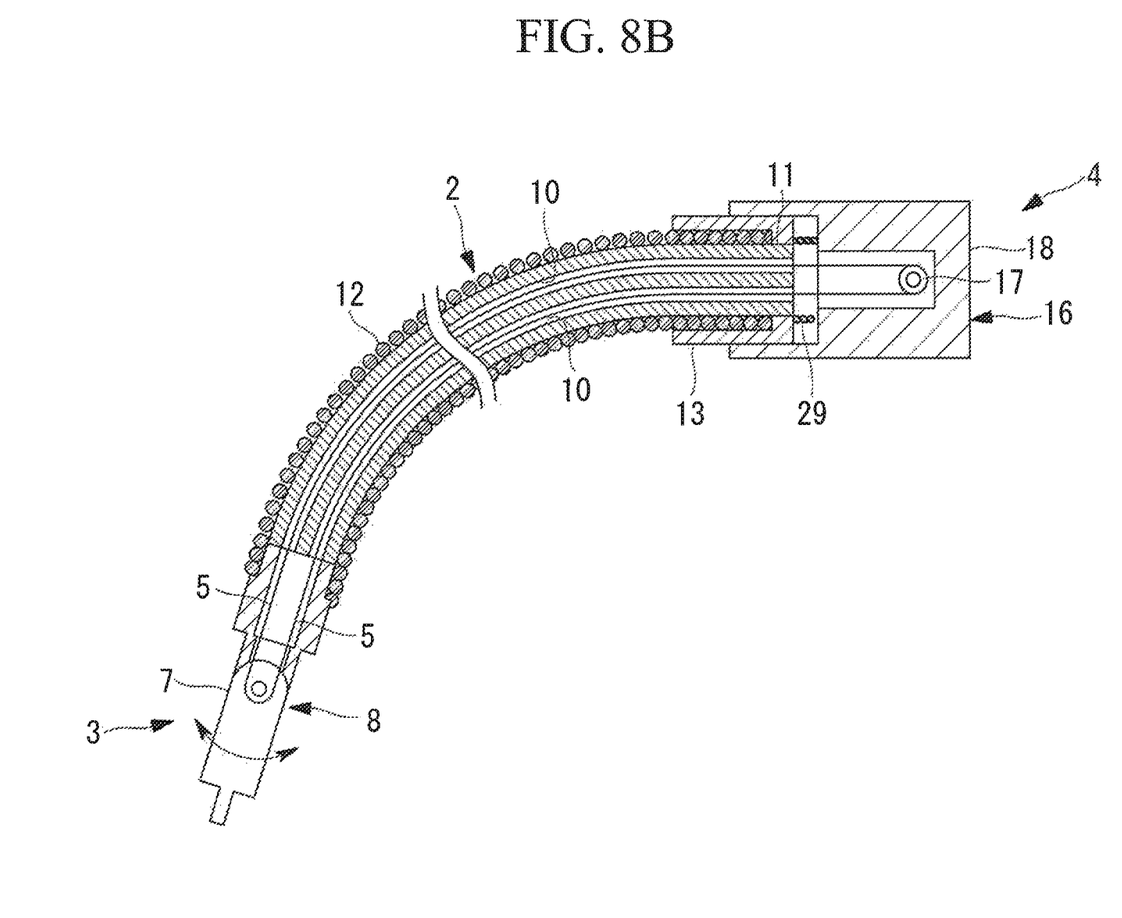
FIG. 8B illustrates another modification of the manipulator in FIG. 1 and is a vertical sectional view showing a state where the manipulator is bent.

According to this configuration, when the long guide member 2 is bent, the compression spring 29 is compressed and the slider 20 is moved, as shown in FIG. 8B.

In this case, the proximal end of the multi-lumen tube 11 fixed to the slider 20 is also moved in accordance with the movement of the slider 20. Because the multi-lumen tube 11 is formed of a resin tube having low rigidity, the multi-lumen tube 11 is expanded when the proximal end thereof is moved. However, by moving the proximal end by the expanded amount, an increase in the path length of the wires 5 can be prevented.

Figure 9A:
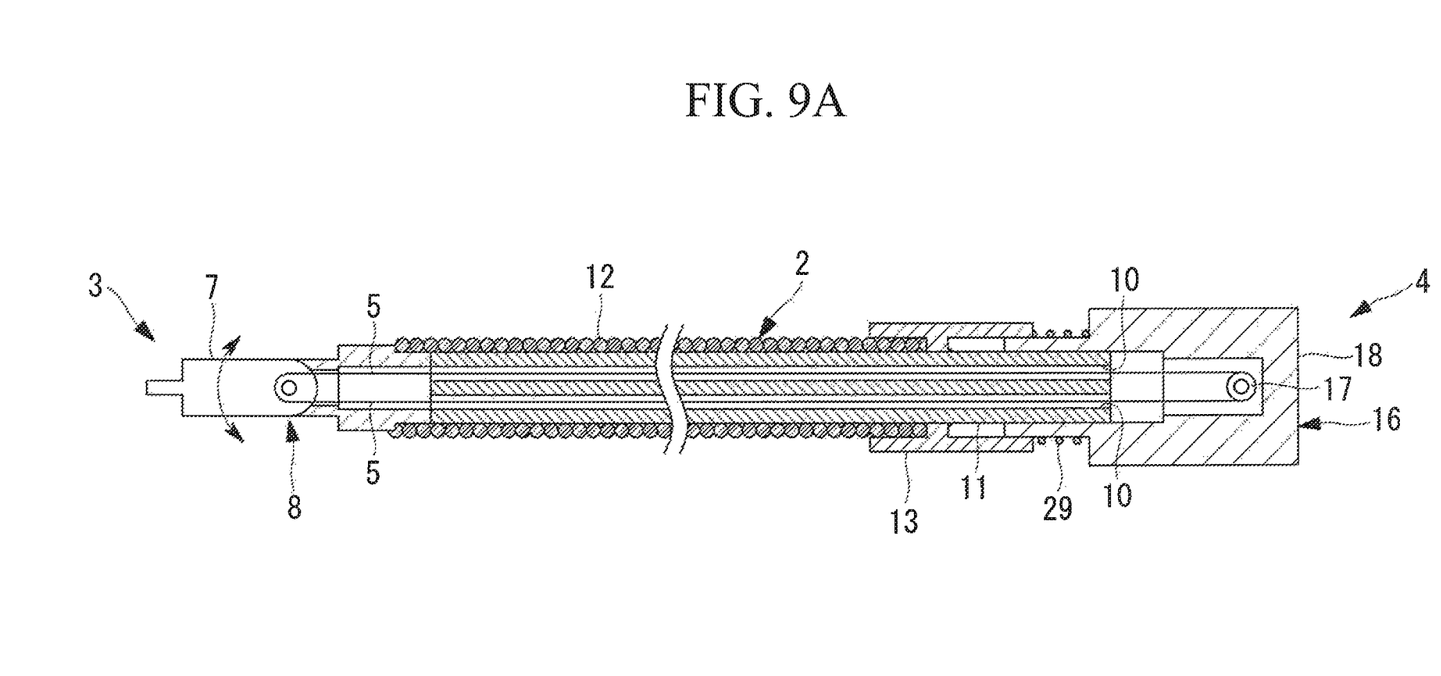
FIG. 9A illustrates yet another modification of the manipulator in FIG. 1 and is a vertical sectional view showing a state where the manipulator extends straight.
Figure 9B:
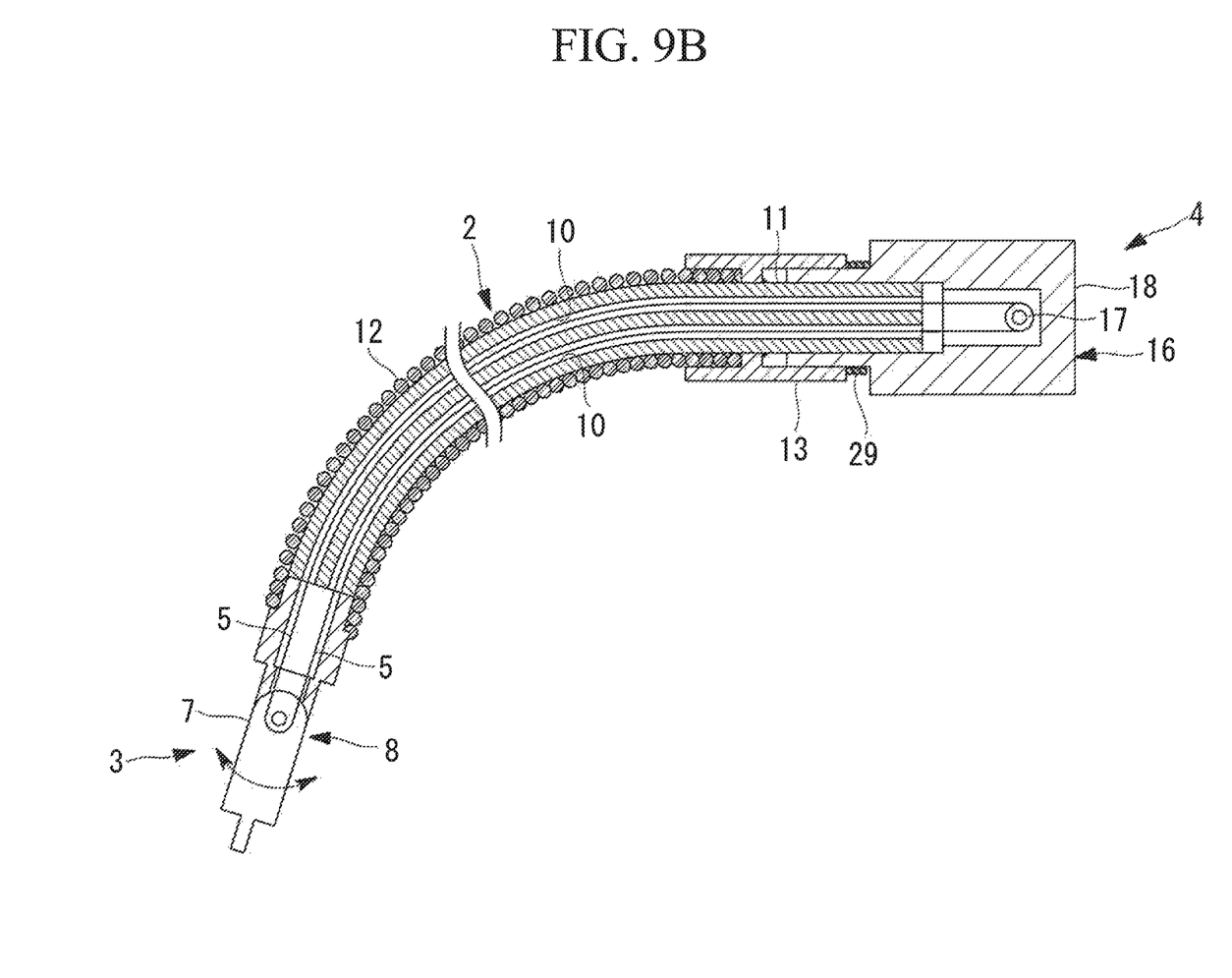
FIG. 9B illustrates yet another modification of the manipulator in FIG. 1 and is a vertical sectional view showing a state where the manipulator is bent.

Furthermore, in this case, the multi-lumen tube 11 may extend into the housing 18 of the driving section 4, as shown in FIGS. 9A and 9B.

Figure 10:
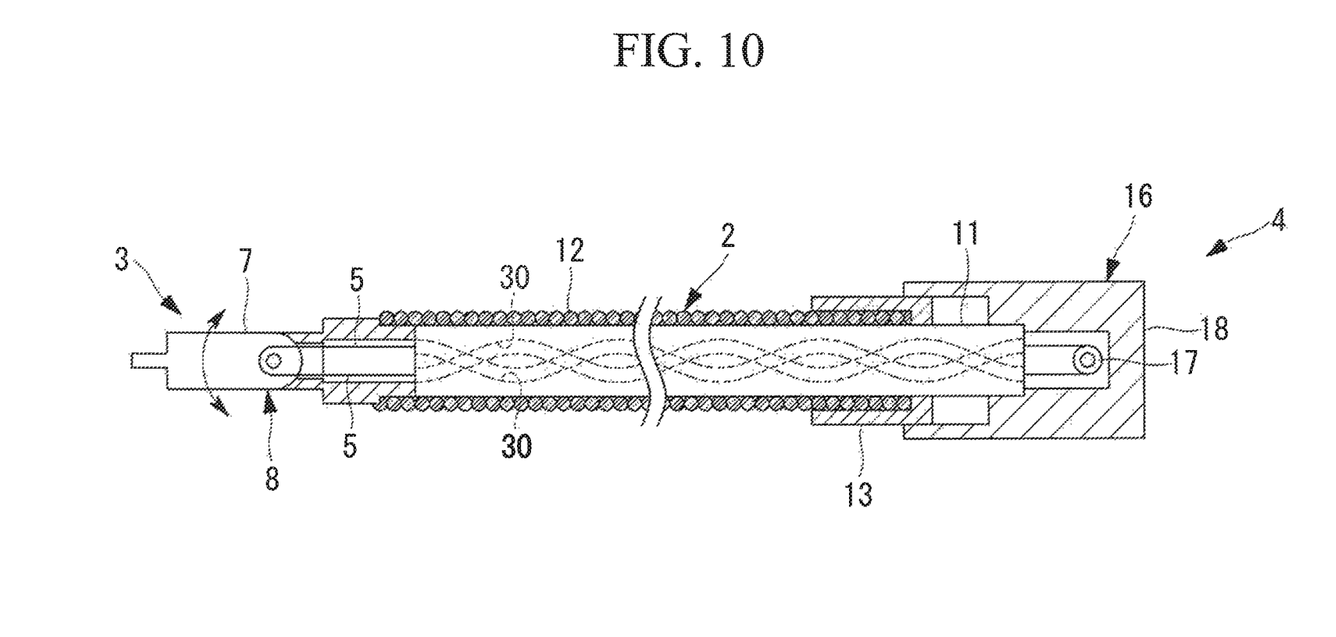
FIG. 10 is a vertical sectional view illustrating a modification of the manipulator in FIG. 1 in which the manipulator includes a multi-lumen tube having twisted lumens as a guide tube.

In this embodiment, the multi-lumen tube 11 has the plurality of lumens 10 formed straight in the longitudinal direction of the multi-lumen tube 11. However, the embodiment is not limited to this configuration. As shown in FIG. 10, lumens 30 that are twisted about the longitudinal axis of the multi-lumen tube 11 may be used.

Accordingly, even if there is a large difference in radii of curvature when a thick multi-lumen tube 11 is used and bent, a change in the length of the lumens 30 caused by the bending process can be suppressed, thereby preventing the path length of the wires 5 from changing.

Although the manipulator-side driving section 16 and the motor unit 15 are attachable to and detachable from each other in this embodiment, the two may be configured as a single unit. In this case, when the manipulator 1 is to be inserted through the channel of the endoscope, the slider 20 may be movable, and the tensile force may be adjusted by moving the slider 20 by using the motor 21a after the insertion process.

Furthermore, as an alternative to the above example in which the movable end member 13 is moved by the movement mechanism 21 equipped with the motor 21a and the linear motion mechanism, the movable end member 13 may be moved by means of a manual movement mechanism 21, such as a dial or a handle.

Although the coil tube 12 is exemplified as an outer sheath in this embodiment, the embodiment is not limited to this configuration. A freely-chosen type of a flexible tube may be used so long as the tube has higher rigidity than the multi-lumen tube 11.

Furthermore, in this embodiment, a pressure sensor (not shown) that detects a pressing force applied to the ball screw 21b by the movement mechanism 21 may be provided.

Accordingly, in a state where the slider 20 is connected to the movable end member 13, the motor 21a of the movement mechanism 21 is actuated so that when the movable end member 13 is pressed, the pressing force detected by the pressure sensor provided in the ball screw 21b increases. Thus, when the pressing force reaches a predetermined pressure, the operation of the movement mechanism 21 is stopped, so that the tensile force of the wires 5 can be properly adjusted.

Although preferred embodiments have been described above, the present invention is not limited to the embodiments and modifications thereof. Additions, omissions, substitutions and other changes in the structure are possible without departing from the spirit of the present invention. The present invention is not limited by the foregoing description but is limited only by the scope of the appended claims.

REFERENCE SIGNS LIST

1 manipulator
2 long guide member
3 movable section (end effector)
4 driving section
5 wire (tensile-force transmitting member)
6 tensile-force adjusting mechanism
10 lumen
11 multi-lumen tube (guide tube)
12 coil tube (outer sheath)
13 movable end member (proximal end section)
14 motor
15 motor unit
17 pulley (power converting section)
20 slider
21 movement mechanism

What is claimed is:

1. A manipulator comprising:
    a housing;
    an end effector movable about a joint;
    a motor configured to generate force so as to move the end effector about the joint;
    a wire configured to transmit the force from the motor to the end effector, a first portion of the wire being operatively connected to the end effector, and a second portion of the wire being operatively connected to the motor;
    a guide tube comprising at least one lumen extended in a longitudinal direction, the at least one lumen configured to guide the wire, a distal end of the guide tube being rotatably connected to the end effector, and a proximal end of the guide tube being fixed to the housing;
    an outer sheath configured to cover an outer surface of the guide tube in a longitudinal direction of the guide tube, the outer sheath having a rigidity higher than a rigidity of the guide tube, a distal end of the outer sheath being fixed to the guide tube and a proximal end of the outer sheath being movable relative to the housing; and
    an adjusting mechanism configured to adjust a position of the proximal end section of the outer sheath relative to the housing in the longitudinal direction of the guide tube so as to adjust a tensile-force generated on the wire.

2. The manipulator according to claim 1, wherein the adjusting mechanism comprising:
    a slider attached to a proximal end of the outer sheath; and
    a movement mechanism configured to move the slider relative to the motor in the longitudinal direction of the guide tube.

3. The manipulator according to claim 2, further comprising:
    a power converting section configured to covert power from the motor to a tensile-force so as to be transmitted by the wire, the power converting section being detachable from the motor,
    wherein the movement mechanism is configured to attach the outer sheath via the slider when the power converting section attaches to the motor.

4. The manipulator according to claim 1, wherein the at least one lumen comprises a plurality of lumens, each of the plurality of lumens extending in a twisted shape about a longitudinal axis in at least a portion of a region of the guide tube.

* * * * *